United States Patent [19]

Barry et al.

[11] 4,454,152

[45] Jun. 12, 1984

[54] METHOXSALEN DOSAGE FORMS

[75] Inventors: Richard H. Barry, Bloomfield; Jack H. Lazarus, Jersey City, both of N.J.

[73] Assignee: Hoffmann-La Roche Inc., Nutley, N.J.

[21] Appl. No.: 332,982

[22] Filed: Dec. 21, 1981

Related U.S. Application Data

[63] Continuation of Ser. No. 147,697, May 7, 1980, abandoned.

[51] Int. Cl.³ .............................................. A61K 31/35
[52] U.S. Cl. ....................................... 424/283; 424/78
[58] Field of Search ................................... 424/283, 78

[56] References Cited

U.S. PATENT DOCUMENTS 3,972,999  8/1976  Tsuk ...................................... 424/78
4,130,568  12/1978  Confolone et al. .............. 424/263 X

OTHER PUBLICATIONS

Chemical Abstracts 85: 99195g (1926).
Chemical Abstracts 81: 96386b (1924).

*Primary Examiner*—Leonard Schenkman
*Attorney, Agent, or Firm*—Jon S. Saxe; Bernard S. Leon; Elizabeth Manning

[57] ABSTRACT

This invention relates to oral dosage forms wherein the active ingredient, methoxsalen, is dispersed in a water-soluble composition containing a polyethylene glycol or mixtures of polyethylene glycols. Dissolution of methoxsalen in gastrointestinal fluids as well as drug absorption are more rapid and higher blood level patterns are achieved with these dosage forms as compared to conventional encapsulated dosage forms.

3 Claims, No Drawings

METHOXSALEN DOSAGE FORMS

This is a continuation of application Ser. No. 147,697 filed May 7, 1980 now abandoned.

BACKGROUND OF THE INVENTION

8-Methoxypsoralen(9-methoxy-7H-furo[3,2g][1]benzopyran-7-one) is a compound of the formula

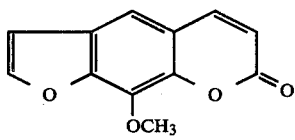

Methoxsalen, as it is more commonly known, has been obtained from natural sources, namely from the fruit of the Ammi Majus Linn plant. See, for example, Fahmy et al., "Ammi Majus Linn. Pharmacognostical Study and Isolation of Crystalline Constituent, Ammoidin", Quart. J. Pharm. and Pharmacol., 20: 281, (1948). In addition, a synthetic process for the preparation of methoxsalen is described in U.S. Pat. No. 4,130,568.

It is known that either the topical application or oral ingestion of psoralens and certain isomers of furocoumarins, have an effect on the responsiveness of human skin to sunlight. These psoralen compounds, including methoxsalen, have long been used in the treatment of skin diseases such as vitiligo which is characterized by a spotty loss of pigmentation of the skin and psoriasis. Methoxsalen has been used, in combination with exposure of the patient to ultra-violet light, to enhance the repigmentation of the skin by increasing melanogenesis. In this treatment of psoriasis (known as PUVA therapy), methoxsalen is given orally in doses adjusted to body weight. Thus, the dose can range from 20 mg for a subject of 50 kg. body weight to 50 mg for a subject of over 80 kg. body weight.

Heretofore, methoxsalen for oral administration was used in the form of gelatin capsules containing about 10 mg of the drug in dry powdered form with such excipients as starch or lactose. The particle size of methoxsalen varied depending on the method and degree of particle size reduction.

Since, in general, the dissolution rate of an orally administered drug, which influences the rate at which the drug enters the blood stream, is related to its particle size, attempts to increase the dissolution rate of methoxsalen, administered in capsules, by reduction in its particle size using such standard procedures as ultrasonic deaggregation (micronization) or comminution were tried. However, since methoxsalen crystals are fluffy, needle-like and reactant to flow, these procedures had several unacceptable features. Thus, in comminution, clogging of the screens is common while in micronization using jet air milling there is considerable loss of drug. Further, the airborne dust resulting from these milling procedures can be hazardous to operating personnel due to the irritant nature of methoxsalen on both the skin and mucous membranes.

Even using the above techniques with their drawbacks, a level of methoxsalen in the blood could only be achieved some two hours after oral administration. The subsequent ultraviolet radiation treatment of a patient had to be deferred until this peak blood-level was achieved, causing much inconvenience to the patient.

The need for an oral dosage form containing methoxsalen in a fine particle size range (e.g. 1–300 microns) is, therefore, apparent.

It was known that the dissolution rate of the antibiotic griseofulvin could be significantly increased by incorporation into melts with a polyethylene glycol (PEG 6000). However, griseofulvin in the solidified melt was in the amorphous form (Chiou and Riegelman, J. Pharm. Sci., 58, No. 12, 1505–1510; 59, No. 7, 937–942; 60, No. 9, 1377–1380). U.S. Pat. No. 3,972,999 discloses a melt of amorphous griseofulvin and certain polyglycolides.

BRIEF DESCRIPTION OF THE INVENTION

This invention is directed to improved methoxsalen oral dosage forms, and methods for their preparation, which utilize a solid dispersion of fine particle sized methoxsalen in an inert carrier or matrix. This solid dispersion combination of the water-insoluble methoxsalen with an inert water-soluble carrier is achieved by dissolving the drug in the glycol(s) or in the molten mixture of the glycols, cooling the resulting admixture to room temperature and milling the composition to a desired particle size range.

The resulting composition can be added alone to gelatin capsules or can be admixed with pharmaceutical adjuvants and either added to capsules or compressed into tablets.

DETAILED DESCRIPTION OF THE INVENTION

Methoxsalen is effective, in compositions for oral use, on the response of human skin to light of ultraviolet wavelength. Thus, methoxsalen is useful in the treatment of such skin diseases as vitiligo and psoriasis.

These methoxsalen compositions comprise dispersions of fine particle-size methoxsalen in an inert carrier or matrix—a dispersion achieved by combining the water-insoluble methoxsalen with an inert water-soluble carrier. The ingredients are melted or fused together and the admixture is cooled to room temperature. The composition is then milled to the desired particle size range.

The inert, water-soluble carrier material dissolves rapidly when exposed to water or gastrointestinal fluids with the release of the finely dispersed drug in micron or submicron particle-size range.

Thus, if orally administered to a subject, the methoxsalen, in micron or submicron particle-size range, is rapidly absorbed systemically. This rapid absorption permits control over the administration and the dosage of the drug in the physician's office rather than in a subject's home or workplace. Further, there is a minimal delay time before initiation of ultraviolet irradiation.

As the inert, water-soluble carrier material, a polyethylene glycol or a mixture of polyethylene glycols has been found to be superior both in dispersing methoxsalen by the fusion method and in increasing the rate of dissolution of methoxsalen in gastrointestinal fluid and, hence, into the blood.

Polyethylene glycols are polyglycols of ethylene glycol—polymers of ethylene oxide and water of the formula $HOCH_2(CH_2OCH_2)_nCH_2OH$ wherein the value of n ranges from 8 to about 200. The molecular weight of the polyethylene glycols can range from approximately 200 to about 9000. The polyethylene glycols are classified by their molecular weight, e.g.

PEG 6000 has an average molecular weight of between 7000 and 9000.

Other polyethylene glycols suitable for use in the compositions of this invention include PEG 400 (average molecular weight of between 380 and 420), PEG 600 (average molecular weight of between 570 and 630), PEG 4000 (average molecular weight of between 3000 and 3700) and the like. Preferred polyethylene glycols are PEG 400, PEG 4000 and PEG 6000.

In addition, methoxy derivatives of polyethylene glycols such as methoxy polyethylene glycol 350, methoxy polyethylene glycol 550 and methoxy polyethylene glycol 750 can be used as the water-soluble carrier material in the compositions of this invention.

The amount of polyethylene glycol in the oral dosage compositions can range, in percent by weight, from about 10 percent to about 97.5 percent.

The concentration of methoxsalen in the compositions can range, in percents by weight based on the total weight of the composition, from about 0.025 percent by weight to about 10.5 percent by weight.

Pharmaceutical adjuvants or excipients which can be admixed with the compositions of this invention include surfactants such as polysorbate 80 (polyethylene sorbitan monooleate, ICI), methylparaben (methylhydroxybenzoate) and propylparaben (propylhydroxybenzoate); diluents such as lactose; binders and disintegrants such as microcrystalline cellulose and the like; glidant-lubricants such as talc, magnesium stearate and the like and food-grade antioxidants such as butylated hydroxytoluene, butylated hydroxyanisole, dl-alpha-tocopherol, ascorbyl palmitate and the like.

The formulations can contain, in percents by weight based on the total weight of the formulation, from about 0.10 to about 5.0 percent surfactant; from about 30 to about 97 percent of a diluent and from about 0.01 to about 20 percent of a glidant-lubricant. The amount of food-grade antioxidant added can range from about 0.01 to about 3.0 percent.

In in vivo studies in dogs, using the compositions of this invention in encapsulated dosage forms, peak levels of methoxsalen in the blood have been obtained in about one-half to one hour as compared to two hours for commercially available conventional encapsulated dosage forms.

Thus, in PUVA therapy, ultraviolet light irradiation could be initiated 2 to 4 times earlier using the compositions of this invention.

The following Examples illustrate the invention.

EXAMPLE 1

Soft gelatin capsules containing the following composition were prepared:

| Ingredient | Mg/capsules |
|---|---|
| Methoxsalen | 10.0 |
| Tween 80 | 1.0 |
| Polyethylene glycol 400 | 388.8 |
| Total | 399.8 |

The methoxsalen was added to the polyethylene glycol in a suitable container and stirred at room temperature until all the crystals were dissolved.

This solution was encapsulated into soft gelatin capsules.

Samples of the above formulations formed clear solutions in in vitro dissolution tests using simulated gastric fluid TS (as described in USP XIX) or simulated intestinal fluid (as described in USP XIX). Drug solubility is about 10 mg per 200 ml of purified water.

Ninety-three percent of the composition dissolved in five minutes and one hundred percent dissolved in ten minutes using the dissolution test described in the United States Pharmacopeia XIX.

EXAMPLE 2

Hard-shell capsules containing the following composition were prepared:

| Ingredient | Mg/capsule A | Mg/capsule B |
|---|---|---|
| Methoxsalen | 10.0 | 10.0 |
| Polyethylene glycol 400 | 15.0 | — |
| Polyethylene glycol 600 | — | 5.0 |
| Polyethylene glycol 6000 | 15.0 | 60.0 |
| Corn Starch | — | 10.0 |
| Talc | — | 10.0 |
| Lactose U.S.P. | 260.0 | — |
| | 300.0 | 95.0 |

The polyethylene glycols were admixed and heated to about 60° C. Methoxsalen was dissolved in the melt by heating the melt up to 105° C.

Lactose or cornstarch/talc were added to a planetary mixer and the methoxsalen-polyethylene glycol mixture was added slowly to the mixer and well-dispersed. The resulting mixture was then milled and screened to an 80–200 mesh powder. This powder was then added to a hard-shell capsule (#2 two-piece) together with a small amount, as needed, of a lubricant such as magnesium stearate or talc.

In an alternate procedure, the melt of methoxsalen and polyethylene glycols was poured, while still liquid, onto a cold surface such as stainless steel or glass plate. The solidified mass was then milled and screened, added to the lactose or cornstarch/talc excipients, mixed well and filled into hard-shell gelatin capsules.

Seventy-five percent of the drug in formula A above, dissolved in five minutes and ninety-eight percent of the drug dissolved in fifteen minutes using the dissolution test described in the United States Pharmacopeia XIX. In comparison, only five percent of the drug dissolved in five minutes using a commercial capsule formulation containing 10 mg of methoxsalen with corn starch. With this same commercial formulation, only 36 percent of the drug dissolved in fifteen minutes and 56 percent dissolved in one hour.

EXAMPLE 3

The following formulations were prepared:

| Ingredient | Mg/tablet A | B | C | D |
|---|---|---|---|---|
| Methoxsalen | 10.0 | 10.0 | 10.0 | 10.0 |
| Polyethylene glycol 400 | — | 3.0 | — | — |
| Polyethylene glycol 4000 | — | — | 90.0 | — |
| Polyethylene glycol 6000 | 90.0 | 27.0 | — | 90.0 |
| Lactose | 247.0 | 247.0 | 247.0 | 207.0 |
| Microcrystalline cellulose | 60.0 | 60.0 | 60.0 | 60.0 |
| Magnesium stearate | 3.0 | 3.0 | 3.0 | 3.0 |
| Corn starch | — | — | — | 30.0 |
| | 410.0 | 350.0 | 410.0 | 400.0 |

In each formulation the polyethylene glycol, or mixtures thereof, were heated to melting (about 60° C.).

The methoxsalen was added to this melt and dissolved therein by heating the melt to about 105° C.

The methoxsalen solution was slowly added to the lactose in a planetary mixer and well dispersed. The resulting mixture was then milled and screened to an 80-200 mesh powder. The microcrystalline cellulose, magnesium stearate and, in Formulation D, corn starch were added and admixed.

The formulations were then compressed into tablets.

EXAMPLE 4

The following formulations were prepared using the procedures described in the above Examples.

| Ingredient | Mg/capsule | | | | |
|---|---|---|---|---|---|
| | E | E-1 | E-2 | F | F-1 |
| Methoxsalen | 10.2 | 10.2 | 10.2 | 10.2 | 10.2 |
| Polyethylene glycol 400 | 15.0 | 15.0 | 15.0 | | |
| Polyethylene glycol 6000 | 15.0 | 90.0 | 90.0 | 90.0 | 90.0 |
| Tween 80 | 1.0 | 1.0 | — | — | 1.0 |
| Lactose, hydrous | 258.8 | 283.8 | 284.8 | 299.8 | 298.8 |
| | 300.0 | 400.0 | 400.0 | 400.0 | 400.0 |

Formulations E and F were compared to a commercial formulation (10 mg. methoxsalen and 390 mg of corn starch per capsule) in in vivo studies in dogs.

For these studies, three dogs were used. They were fasted for 24 hours prior to administration of the drugs. Methoxsalen, in the different formulations, was administered in capsule form per os.

Blood specimens were obtained over a period of from 0 hour to 48 hours after drug administration. The results are tabulated below.

TABLE 1

| | Methoxsalen Blood Levels | | | | | | | |
|---|---|---|---|---|---|---|---|---|
| | Blood Levels (μg/ml) | | | | | | | |
| | A. Dog 1 | | | B. Dog 2 | | | C. Dog 3 | |
| Formulation→ | Commercial | E | F | Commercial | E | F | Commercial | E | F |
| Elapsed Time | | | | | | | | | |
| 1 min. | — | — | — | — | — | — | — | — |
| 5 min. | — | — | — | — | — | | | | |
| 10 min. | n.m | 0.1 | 0.06 | n.m | n.m | n.m | 0.49 | n.m |
| 20 min. | n.m | 0.81 | 0.14 | 0.48 | n.m | 0.52 | 2.42 | 0.38 |

TABLE 1-continued

| | Methoxsalen Blood Levels | | | | | | | |
|---|---|---|---|---|---|---|---|---|
| | Blood Levels (μg/ml) | | | | | | | |
| | A. Dog 1 | | | B. Dog 2 | | | C. Dog 3 | |
| Formulation→ | Commercial | E | F | Commercial | E | F | Commercial | E | F |
| 30 min. | 0.21 | 1.37 | 0.61 | 0.80 | 0.58 | 1.09 | 2.28 | 0.57 |
| 45 min. | 0.73 | 1.25 | 0.84 | 1.10 | 2.09 | 1.35 | 1.63 | 3.09 |
| 1 hour | 1.13 | 1.22 | 1.67 | 1.28 | 2.01 | 1.51 | 1.32 | 3.11 |
| 1.5 hours | 1.18 | 1.15 | 2.23 | 1.25 | 1.97 | 1.23 | 0.98 | 1.62 |
| 2 hours | 1.13 | 1.07 | 1.84 | 1.35 | 1.54 | 1.21 | 0.96 | 1.43 |
| 6 hours | 0.50 | 0.51 | 0.81 | 0.77 | 0.59 | 0.72 | 0.56 | 0.70 |
| 10 hours | 0.34 | 0.36 | 0.39 | 0.51 | 0.33 | 0.29 | 0.32 | 0.39 |
| 24 hours | n.m | n.m | 0.04 | 0.08 | 0.02 | n.m | n.m | 0.06 |
| 30 hours | 0.04 | n.m | n.m | n.m | n.m | n.m | n.m | n.m |
| 48 hours | n.m | n.m | n.m | n.m | n.m | n.m | n.m | n.m | n.m = non-measurable (<0.01 μg/ml blood)

We claim:

1. A method of treating a subject afflicted with psoriasis or vitiligo which method comprises
   (a) administering to the subject an oral dosage composition comprising a solution of an amount of methoxsalen effective for the treatment of psoriasis or vitiligo in about 10 to about 97.5 percent by weight based on the total weight of the composition of a polyethylene glycol or a mixture of polyethylene glycols which polyethylene glycol or mixture is fluid at room temperature contained within a capsule.
   (b) waiting a sufficient time to obtain a peak blood level of methoxsalen in the subject, and
   (c) irradiating the subject with ultraviolet light.

2. An oral dosage composition in a unit dosage form comprising a solution of an amount of methoxsalen effective for the treatment of psoriasis or vitiligo in about 10 to about 97.5 percent by weight based on the total weight of the composition of a polyethylene glycol or a mixture of polyethylene glycols which polyethylene glycol or mixture is fluid at room temperature contained within a capsule.

3. An oral dosage composition in unit dosage form comprising a solution, which in percent by weight based on the total weight of the composition, is from about 0.025% to about 10.5% of methoxsalen and from about 10% to about 97.5% of a polyethylene glycol or a mixture of polyethylene glycols which polyethylene glycol or mixture is fluid at room temperature, contained within a capsule.

* * * * *